United States Patent
Giffels et al.

(10) Patent No.: US 6,288,262 B2
(45) Date of Patent: Sep. 11, 2001

(54) PROCESS FOR THE PREPARATION OF 2-METHOXYETHOXY-BENZENES AND NOVEL 2-METHOXYETHOXY-BENZYL CYANIDES

(75) Inventors: Guido Giffels, Bonn; Claus Dreisbach, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/774,215

(22) Filed: Jan. 30, 2001

(30) Foreign Application Priority Data

Feb. 9, 2000 (DE) .............................. 100 05 570

(51) Int. Cl.[7] .......................... C07C 255/00; C07C 47/28
(52) U.S. Cl. .......................... 558/423; 558/426; 568/442
(58) Field of Search ................... 558/423, 426; 568/442

(56) References Cited

FOREIGN PATENT DOCUMENTS

98/37079    8/1998   (WO) .

OTHER PUBLICATIONS

J. Med. Chem., (month unavailable) 1982, 25, pp. 435–440, Ren–li Li, Corwin Hansch and Bernard T. Kaufman, A Comparison of the Inhibitory Action of 5–(Substituted–benzyl)–2,4–Diaminopyrimidines on Dihydrofolate Reductase from Chicken Liver with That from Bovin Liver.

Can. J. Chem., 73 (month unvailble) 1995, pp. 566–572, G.W. Buchanan, A Moghimi, V.M. Reynolds and K. Bourque, Dicyclohexylethyleneglycol, –diethyleneglycol, –triethyleneglycol, and related monosubstituted cylohexanes. Conformational analysis using low–temperature $^{13}$C and $^{1}$H NMR spectroscopy.

*Primary Examiner*—Joseph K. McKane
*Assistant Examiner*—Joseph Murray
(74) *Attorney, Agent, or Firm*—Joseph C. Gil; Diderico van Eyl

(57) ABSTRACT

2-Methoxyethoxy-benzenes are obtained in an advantageous manner from the corresponding phenol compounds by reaction with 2-chloroethyl methyl ether if the process is carried out without the addition of a strong solvent at temperatures above 95° C. and under pressure. The present invention also relates to novel 2-methoxyethoxybenzyl cyanides.

10 Claims, No Drawings

PROCESS FOR THE PREPARATION OF 2-METHOXYETHOXY-BENZENES AND NOVEL 2-METHOXYETHOXY-BENZYL CYANIDES

FIELD OF THE INVENTION

The present invention relates to an advantageous process for the preparation of 2-methoxyethoxy-benzenes from corresponding phenols and to novel 2-methoxyethoxy-benzyl cyanides.

BACKGROUND OF THE INVENTION

Alkoxybenzyl cyanides, such as 4-(2-methoxyethoxy)-benzyl cyanide, are active ingredient intermediates which make a series of subsequent products, such as the corresponding phenylacetic acids, amides and amines, accessible. For 2-(4-(2-methoxyethoxy)-phenyl)-ethylamine, which is readily obtainable from 4-(2-methoxyethoxy)-benzyl cyanide, uses as a building block in the synthesis of pharmacologically effective substances are known (WO 98/37079). However, the synthesis of this amine has hitherto not been described in the literature. The 4-(2-methoxyethoxy)-benzyl cyanide according to the invention permits simple access to this synthesis building block.

It is known that 3- and 4-(2-methoxyethoxy)-benzaldehyde can be prepared by boiling at reflux 3- or 4-hydroxybenzaldehyde respectively with 2-chloroethyl methyl ether in dimethylformamide in the presence of potassium carbonate. This gives yields of 60.5 and 75.5% of theory respectively (see J. Med. Chem. 25, 440 (1982) method B). A disadvantage is firstly the at times unsatisfactory yield and, secondly, the use of a costly strong polar solvent, which requires considerable expenditure with respect to industrial hygiene and cannot be completely recycled.

In a process for the preparation of 2-methoxyethoxy-benzene (referred to there as 1-methyl-4-phenyl-ethylene glycol), phenol is reacted with 2-bromoethyl methyl ether in acetonitrile, also a costly strong polar solvent, in the presence of potassium carbonate by boiling at reflux (see Can. J. Chem. 73, 572 (1995)). In addition to the expenditure for the provision of the bromine compound and the disadvantages arising by virtue of the use of acetonitrile (which are similar to those in the case of the use of dimethylformamide), the yield achieved of only 26% is entirely unsatisfactory.

There is therefore still a need for a process for the preparation of 2-methoxyethoxybenzenes which produces the desired products in good yields in a simple and cost-effective manner.

DESCRIPTION OF THE INVENTION

We have now found a process for the preparation of 2-methoxyethoxy-benzenes from the corresponding phenol compounds by reaction with 2-chloroethyl methyl ether, which is wherein the process is carried out without the addition of a strong polar solvent at temperatures above 95° C. and under pressure.

Phenol compounds which can be used are, for example, those of the formula (I)

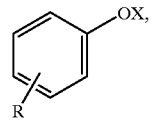

in which
X is H, an alkali metal or a half-equivalent of an alkaline earth metal and
R is H, CHO, $CH_2CN$, CN, $NO_2$, $C_1$–$C_{10}$-alkyl, $C_1$–$C_{10}$-alkoxy, $(CH_2)_x$—OH where x is 1 to 5, halogen or halogeno-$C_1$–$C_{10}$-alkyl.

In formula (D, the radical R is preferably in the ortho- or para-position, in particular in the para-position, relative to the OX group.

In formula (I), X is preferably H, Na or K.

If, in formula (I) X is H, the process according to the invention is carried out in the presence of a base, otherwise the presence of a base is not obligatory, but advantageous. Examples of suitable bases are hydrides, hydroxides, oxides, alkoxides, hydrogen-carbonates and carbonates of alkali metals and alkaline earth metals. Preference is given to potassium carbonate and sodium carbonate.

If the process is carried out in the presence of bases, 0.5 to 10 equivalents preferably 0.9 to 2 equivalents, of one or more bases can, for example, be used per mole of phenol compound of the formula (I). In formula (I), R is preferably H, CHO, $CH_2CN$ or $CF_3$.

2-Chloroethyl methyl ether can be used, for example, in amounts of from 1 to 50 mol per mole of phenol compound. This amount is preferably 2 to 20 mol.

An essential feature of the process according to the invention is that no strong polar solvent is used. Strong polar solvents, for example, comprise amides such as dimethyl formamide, dimethylacetamide and N-methyl-pyrrolidone, sulfones such as dimethylsulfon, sulfoxides such as dimethylsulfoxide, cyclic sulfones such as tetramethylene sulfene and nitrites such as benzonitrile and acetonitrile. Examples of solvents which might be present in the process of the invention can be an excess of 2-chloroethyl methyl ether or weakly polar and no polar solvents such as toluene, xylenes, chlorobenzene and dichlorobenzenes. An excess of 2-chloroethyl methyl ether is preferred.

The process according to the invention can, for example, be carried out at temperatures in the range 95 to 300° C. Preference is given to carrying out the reaction at 100 to 200° C., in particular at 130 to 170° C.

A further essential feature of the process according to the invention is that it is carried out under pressure. The pressure can, for example, be in the range 1 to 60 bar.

The process is preferably carried out in a sealed vessel at the pressure which is automatically established at the respective reaction temperature. At the particularly preferred reaction temperatures, pressures below 10 bar, frequently below 6 bar, arise.

The reaction of the phenol compounds with the 2-chloroethyl methyl ether is generally complete after 3 to 20 hours. It is of course advantageous to stir the mixture during the reaction.

The reaction mixture present after the process according to the invention has been carried out can be worked up, for example, by cooling it, removing the solid constituents of the reaction mixture (essentially chlorides and in some instances bases) e.g. by filtration, and, from the filtrate, obtaining firstly optionally present excessive 2-chloroethyl methyl ether and/or solvents and then the prepared 2-methoxyethoxybenzenes, e.g. by fractional distillation. The separated-off 2-chloroethyl methyl ether is of high purity, meaning that it can be recycled completely and repeatedly.

It is possible for the prepared 2-methoxyethyl-benzene in some cases still to comprise small amounts of unreacted phenol compound. If desired, these can be removed, e.g. by dilution with an inert solvent, e.g. toluene, and extraction with a strong base, e.g. aqueous sodium hydroxide solution.

The 2-methoxyethoxy-benzenes to be prepared according to the invention correspond, for example, to the formula (II)

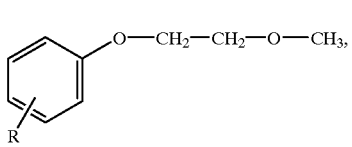

(II)

in which
R has the meaning given in the case of formula (I).

The process according to the invention has a number of advantages. For example, the yields and purities of the 2-methoxyethoxy-benzenes which may be obtained are high. The yield is often around 90% of theory and often considerably greater than in accordance with the prior art. The purity of the 2-methoxyethoxy-benzenes obtained is frequently 98% and can reach almost 100%. Costly solvents which require high expenditure in terms of industrial hygiene and which cannot be completely recycled, such as dimethylformamide, are not required. To carry out the process according to the invention, stirred reactors designed for pressures of from 1 to 60 bar suffice. The reaction times are generally shorter than in the case of known processes.

These advantages are surprising since the process according to the invention is carried out at similarly high temperatures as in accordance with the prior art. However, here as well as there, secondary reactions must be expected at similar temperatures, which adversely affect the yield and purity of the prepared products, in particular where phenol compounds of the formula (I) where R does not equal H are used. Surprisingly, in the case of the process according to the invention, the yields and purities are better. In addition, it had not been predicted that the omission of the strongly polar solvent hitherto regarded as necessary would not have a negative effect.

The present invention further relates to novel 2-methoxyethoxy-benzyl cyanides of the formula (III)

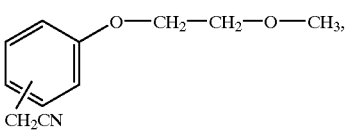

(III)

in which the CH$_2$CN group is arranged in the ortho- or para-position relative to the 2-methoxyethoxy group.

The preparation and use of these novel compounds has been described above. The novel compounds enrich the technology in particular by virtue of the fact that novel species from the group of 2-methoxyethoxy-benzenes are made available. This broadens the range of intermediates and opens up preparation possibilities for potential novel active ingredients.

In addition, by hydrogenating 4-(2-methoxyethoxy)-benzyl cyanide, e.g. in the presence of Raney nickel and ammonia in isopropanol at 80° C. and a hydrogen pressure of 50 bar, it is possible to obtain 2-(4-(2-methoxyethoxy)-phenyl)-ethylamine in yields above 90%. Despite a mention in WO 98/37079, this amine was hitherto unavailable because no preparation process was known.

4-(2-Methoxyethoxy)-benzyl cyanide is also accessible by chloromethylation of 1-(2-methoxyethoxy)-benzene to 4-(2-methoxy-ethoxy)benzyl chloride and reaction of the latter with cyanide.

The invention is further described in the following illustrative examples in which all parts and percentages are by weight unless otherwise indicated.

EXAMPLES

Example 1

1-(2-Methoxyethoxy)-benzene

A 3 l autoclave with paddle stirrer was firstly charged with 209 g of sodium phenoxide and 10 g of potassium carbonate in 1100 g of 2-chloroethyl methyl ether. The autoclave was sealed, flushed with nitrogen and heated to 150° C. over the course of 1 hour with stirring. The mixture was stirred for 10 hours at this temperature, the internal pressure rising to a maximum of 5.4 bar. The mixture was then cooled, and the salts present were filtered off and then washed with 48.5 g of 2-chloroethyl methyl ether. The combined filtrates were evaporated under reduced pressure, giving 808.8 g of 2-chloroethyl methyl ether with a purity of 98.6% (GC area %) as distillate. The liquid residue, which, according to GC, still contained about 2% of phenol, was diluted with 387 g of toluene and washed with 2×500 g of 10% strength aqueous sodium hydroxide solution. The organic phase was then evaporated on a rotary evaporator, and the residue of 259.6 g was fractionally distilled under reduced pressure. At 9 mbar, 213 g of pure product in the form of a clear, colorless liquid passed over at a head temperature of from 90 to 93° C., corresponding to a yield of 78%. Using GC, no by-products at all could be found.

Example 2

4-(2-Methoxyethoxy)-benzaldehyde 36.63 g of 4-hydroxybenzaldehyde were stirred with 60 g of potassium carbonate and 189.08 g of 2-chloroethyl methyl ether in a 0.7 l autoclave for 10 hours at 150° C. Filtration, washing with 50 g of 2-chloroethyl methyl ether and removal by distillation of the excess 2-chloroethyl methyl ether as in Example 1 gave 50.8 g of product in the form of a clear, reddish liquid and 106.23 g of 2-chloroethyl methyl ether with a purity of 99.8% according to GC. The product had a content of 98.3% by weight according to HPLC, corresponding to a yield of 92.4%.

Example 3

4-(2-Methoxyethoxy)-benzaldehyde 219.8 g of 4-hydroxybenzaldehyde were stirred with 270 g of potassium carbonate and 1134 g of 2-chloroethyl methyl ether in a 3 l autoclave for 12 hours at 150° C. Filtration, washing with 46.1 g of 2-chloroethyl methyl ether and removal by distillation of the excess 2-chloroethyl methyl ether as in Example 1, gave 319.9 g of crude product as red-brown liquid and 819.2 g of 2-chloroethyl methyl ether with a purity of 99.4% (GC). Fractionation of the crude product at 1 mbar gave, at 117 to 120° C., 281.2 g of high-purity product in the form of a clear, colorless liquid, corresponding to a yield of 87%.

Example 4

4-(2-Methoxyethoxy)-benzaldehyde 65 g of 6-hydroxybenzaldehyde was suspended in 350 g of 2-chloroethyl methyl ether and admixed with 96 g of 30% strength sodium methoxide solution in methanol. The methanol was distilled off, and the resulting suspension was stirred in an autoclave at 150° C. for 10 hours. Filtration, washing with 10.8 g of 2-chloroethyl methyl ether and removal by distillation of the excess reagent gave 237.5 g of 2-chloroethyl methyl ether as distillate in a purity of 99% according to GC and 82.7 g of crude product as a reddish-brown liquid. The crude product comprised, in addition to residual 4-hydroxybenzaldehyde, 87.9% by weight of the product according to HPLC analysis, corresponding to a yield of 76% of theory.

Example 5

4-(2-Methoxyethoxy)-benzyl cyanide 30 g of 4-hydroxybenzyl cyanide were stirred with 34.25 g of potassium carbonate and 189.1 g of 2-chloroethyl methyl ether in a 0.7 l autoclave at 150° C. for 10 hours. Filtration, washing with 20.5 g of 2-chloroethyl methyl ether and removal by distillation of the excess 2-chloroethyl methyl ethers as in Example 1 gave 139.3 g of 2-chloroethyl methyl ether as distillate with a content of 98.4% (GC) and 41.7 g of product in the form of an oil which crystallized spontaneously upon standing. The product revealed no impurities in the GC-MS and $^1$H-NMR. The $^1$H-NMR investigation (CDCl$_3$, 400 MHz) gave the following characteristic signals: δ=3.45 (s, 3H); 3.68 (s, 2H); 3.77 (t, 2H); 4.12 (t, 2H); 6.91 (2H) and 7.23 (2H). The yield was 96.8%.

Example 6

4-(2-Methoxyethoxy)-benzaldehyde 157 g of 4-hydroxybenzaldehyde were initially introduced under nitrogen dissolved in 540 ml of methanol. 51.4 g of sodium hydroxide were added to the solution in portions over 1.5 hours (exothermic). The mixture was then stirred for a further 1.5 hours, then the solvent was distilled off. The residue (4-hydroxybenzaldehyde Na salt, 212 g) was stirred with 810 g of 2-chloroethyl methyl ether and 1 g of potassium iodide in a 3 liter autoclave at 150° C. for 10 hours. The contents of the autoclave were then removed, the autoclave was washed with 47.2 g of 2-chloroethyl methyl ether and the 2-chloroethyl methyl ether was distilled off. 689.3 g of 2-chloroethyl methyl ether with a GC content of 99.24 area% were recovered. The residue was taken up in 340 ml of toluene and extracted with 500 g of 10% strength aqueous sodium hydroxide solution. 499 g of organic phase were obtained, and the aqueous phase was discarded. Analysis of the organic phase revealed a content of 42.5% by weight of product, corresponding to a yield of 91.5%.

Although the present invention has been described in detail with reference to certain preferred versions thereof, other variations are possible. Therefore, the spirit and scope of the appended claims should not be limited to the description contained therein.

What is claimed is:

1. Process for the preparation of a 2-methoxyethoxy-benzene comprising reacting (i) a phenol compound corresponding to the 2-methoxyethoxy-benzene with (ii) 2-chloroethyl methyl ether, wherein the process is carried out under pressure at a temperature that is above 95° C. and without the addition of a strong polar solvent.

2. Process according to claim 1, wherein the phenol compound has a formula (I)

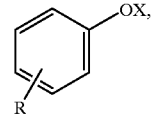

(I)

wherein
X is H, an alkali metal or a half-equivalent of an alkaline earth metal and
R is H, CHO, CH$_2$CN, CN, NO$_2$, C$_1$–C$_{10}$-alkyl, C$_1$–C$_{10}$-alkoxy, (CH$_2$)$_x$—OH where x is 1 to 5, halogen or halogeno-C$_1$–C$_{10}$-alkyl.

3. Process according to claim 2, wherein in formula (I), the radical R is in the ortho- or para-position relative to the OX group.

4. Process according to claim 1, wherein the process is carried out in the presence of a base.

5. Process according to claim 1, wherein 2-chloroethyl methyl ether is used in an amount that ranges from about 1 to about 50 mol per mole of the phenol compound.

6. Process according to claim 1, wherein the process is cared out at a temperature that ranges from about 95 to about 300° C.

7. Process according to claim 1, wherein the process is carried out a pressure that ranges from about 1 to about 60 bar.

8. Process according to claim 1, wherein the reaction mixture present after the reaction is worked up by cooling the reaction mixture, solid constituents are removed by filtration and, from the filtrate, excess 2-chloroethyl methyl ether is obtained first and the 2-methoxy-ethoxy-benzene is obtained by fractional distillation.

9. Process according to claim 1, wherein the reaction is carried out in the presence of a weakly polar or non polar solvent.

10. Compounds of the formula (III)

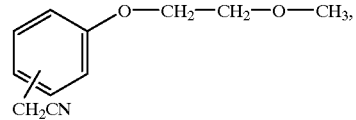

(III)

in which the CH$_2$CN group is arranged in the ortho- or para-position relative to the 2-methoxyethoxy group.

* * * * *